United States Patent
Funabasama

(10) Patent No.: US 11,443,497 B2
(45) Date of Patent: Sep. 13, 2022

(54) MEDICAL IMAGE PROCESSING APPARATUS, MEDICAL IMAGE PROCESSING SYSTEM, MEDICAL IMAGE PROCESSING METHOD, AND RECORDING MEDIUM

(71) Applicant: CANON MEDICAL SYSTEMS CORPORATION, Otawara (JP)

(72) Inventor: Shintaro Funabasama, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 52 days.

(21) Appl. No.: 16/985,316

(22) Filed: Aug. 5, 2020

(65) Prior Publication Data
US 2021/0043010 A1  Feb. 11, 2021

(30) Foreign Application Priority Data
Aug. 6, 2019  (JP) .............................. JP2019-144087

(51) Int. Cl.
*G06T 15/00* (2011.01)
*G06T 19/20* (2011.01)
(Continued)

(52) U.S. Cl.
CPC .............. *G06T 19/20* (2013.01); *A61B 6/032* (2013.01); *A61B 6/505* (2013.01); *G16H 30/40* (2018.01);
(Continued)

(58) Field of Classification Search
CPC ..... G06T 7/11; G06T 19/20; G06T 2219/008; G06T 2219/2021; G06T 2210/41;
(Continued)

(56) References Cited

U.S. PATENT DOCUMENTS 10,456,263 B2 * 10/2019 Bojarski .................. A61F 2/40
11,013,560 B2 *  5/2021 Lang ...................... A61B 34/74
(Continued)

FOREIGN PATENT DOCUMENTS

JP      2010-148590 A     7/2010
JP      2013-240534 A    12/2013

OTHER PUBLICATIONS

Zheng G, Schumann S. 3D reconstruction of a patient-specific surface model of the proximal femur from calibrated x-ray radiographs: A validation study a. Medical physics. Apr. 2009;36(4): 1155-66.*

(Continued)

*Primary Examiner* — Phu K Nguyen
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to set a curved plane between a first bone region and a second bone region included in a joint, in three-dimensional medical image data obtained by imaging the joint including at least the first bone region and the second bone region. The processing circuitry is configured to reshape at least one of the first and the second bone regions along extension of the curved plane to obtain a reshaped bone region. The processing circuitry is configured to generate display-purpose image data on the basis of the reshaped bone region resulting from the reshaping.

12 Claims, 15 Drawing Sheets

(51) Int. Cl.
*G16H 30/40* (2018.01)
*G16H 50/30* (2018.01)
*G16H 50/50* (2018.01)
*A61B 6/03* (2006.01)
*A61B 6/00* (2006.01)
*G16H 50/20* (2018.01)

(52) U.S. Cl.
CPC ............ *G16H 50/20* (2018.01); *G16H 50/30* (2018.01); *G16H 50/50* (2018.01); *G06T 2200/04* (2013.01); *G06T 2210/41* (2013.01); *G06T 2219/2021* (2013.01)

(58) Field of Classification Search
CPC ..... G06T 2200/04; A61B 17/15; A61B 6/032; A61B 6/505; G06F 3/011; G16H 50/20; G16H 50/50; G16H 50/30; G16H 30/40
USPC ......................................................... 345/418
See application file for complete search history.

(56) References Cited

U.S. PATENT DOCUMENTS

| | | | | |
|---|---|---|---|---|
| 2011/0257518 | A1* | 10/2011 | Buly | A61B 5/103 |
| | | | | 600/427 |
| 2017/0119531 | A1* | 5/2017 | Bojarski | A61F 2/3859 |
| 2017/0367716 | A1* | 12/2017 | Park | A61B 17/157 |
| 2017/0367766 | A1* | 12/2017 | Mahfouz | A61B 34/20 |
| 2021/0022810 | A1* | 1/2021 | Mahfouz | A61F 2/30942 |
| 2021/0315642 | A1* | 10/2021 | Mcguan | G16H 20/40 |
| 2021/0322148 | A1* | 10/2021 | Mitra | A61B 34/20 |

OTHER PUBLICATIONS

Baka N, Kaptein BL, de Bruijne M, van Walsum T, Giphart JE, Niessen WJ, Lelieveldt BP. 2D-3D shape reconstruction of the distal femur from stereo X-ray imaging using statistical shape models. Medical image analysis. Dec. 1, 2011;15(6):840-50.*
Harrysson OL, Hosni YA, Nayfeh JF. Custom-designed orthopedic implants evaluated using finite element analysis of patient-specific computed tomography data: femoral-component case study. BMC musculoskeletal disorders. Dec. 2007;8(1):1-0.*
Chandra SS, Xia Y, Engstrom C, Crozier S, Schwarz R, Fripp J. Focused shape models for hip joint segmentation in 3D magnetic resonance images. Medical image analysis. Apr. 1, 2014;18(3):567-78.*
Nakao M, Aso S, Imai Y, Ueda N, Hatanaka T, Shiba M, Kirita T, Matsuda T. Automated planning with multivariate shape descriptors for fibular transfer in mandibular reconstruction. IEEE transactions on biomedical engineering. Oct. 26, 2016;64(8):1772-85.*
Romero Sánchez, José Javier. "Computational medical imaging for total knee arthroplasty using visualitzation toolkit." Master's thesis, Universitat Politècnica de Catalunya, 2015.*
Cevidanes LH, Tuckers, Styner M, Kim H, Chapuis J, Reyes M, Proffit W, Turvey T, Jaskolka M. Three-dimensional surgical simulation. American journal of orthodontics and dentofacial orthopedics. Sep. 1, 2010;138(3):361-71.*
Tsai et al, Volume Manipulation Based on 3D Reconstructed Surfaces for Joint Function Evaluation and Surgery Simulation. The 40th Annual International Conference of the IEEE Engineering in Medicine and Biology Society (EMBC) Jul. 18, 2018 . https://ieeexplore.ieee.org/stamp/stamp.jsp?tp=&arnumber=8512449.*

* cited by examiner

FIG.13
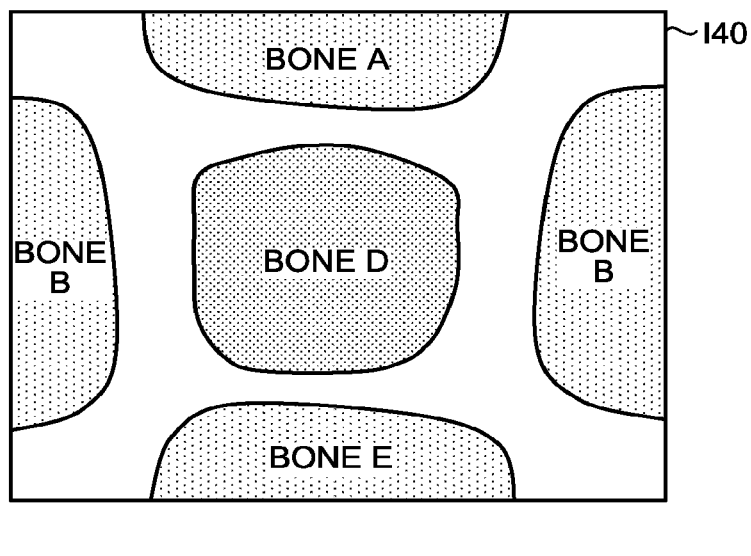
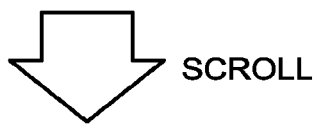
SCROLL
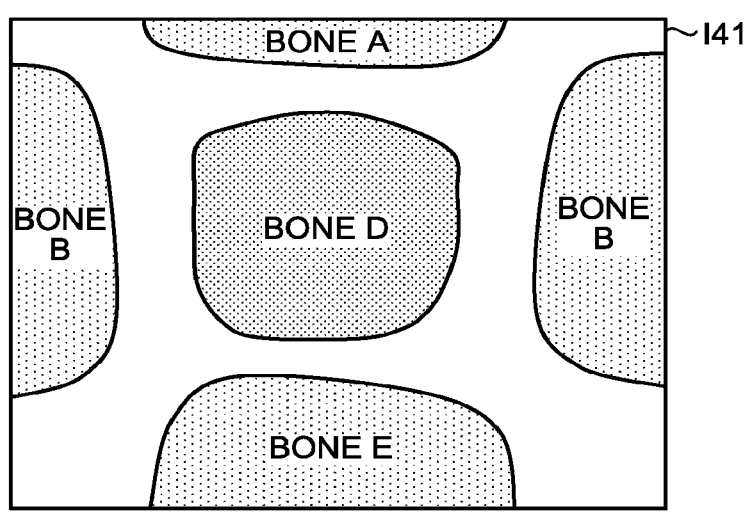

MEDICAL IMAGE PROCESSING APPARATUS, MEDICAL IMAGE PROCESSING SYSTEM, MEDICAL IMAGE PROCESSING METHOD, AND RECORDING MEDIUM

CROSS-REFERENCE TO RELATED APPLICATIONS

This application is based upon and claims the benefit of priority from Japanese Patent Application No. 2019-144087, filed on Aug. 6, 2019; the entire contents of which are incorporated herein by reference.

FIELD

Embodiments described herein relate generally to a medical image processing apparatus, a medical image processing system, a medical image processing method, and a recording medium.

BACKGROUND

Conventionally, bones structuring joints are observed by analyzing three-dimensional medical image data. For example, by using anatomical characteristic information of a joint to be analyzed, regions of a plurality of bones structuring the joint are extracted from X-ray Computed Tomography (CT) image data, so as to generate and display a rendering image of the extracted bones. For this technique, a dedicated program is developed for each type of joint, such as one for the knee joint and another for the hip joint.

BRIEF DESCRIPTION OF THE DRAWINGS

FIG. 13 is another drawing for explaining the process performed by the medical image processing apparatus according to the second modification example;

DETAILED DESCRIPTION

A medical image processing apparatus according to an embodiment includes processing circuitry. The processing circuitry is configured to set a curved plane between a first bone region and a second bone region included in a joint, in three-dimensional medical image data obtained by imaging the joint including at least the first bone region and the second bone region. The processing circuitry is configured to reshape at least one of the first and the second bone regions along extension of the curved plane to obtain a reshaped bone region. The processing circuitry is configured to generate display-purpose image data on the basis of the reshaped bone region resulting from the reshaping.

Exemplary embodiments of a medical image processing apparatus, a medical image processing system, a medical image processing method, and a record medium will be explained below, with reference to the accompanying drawings. Possible embodiments are not limited to the embodiments described below. Further, the description of each of the embodiments is, in principle, similarly applicable to any other embodiment.

Embodiments

Figure 1:
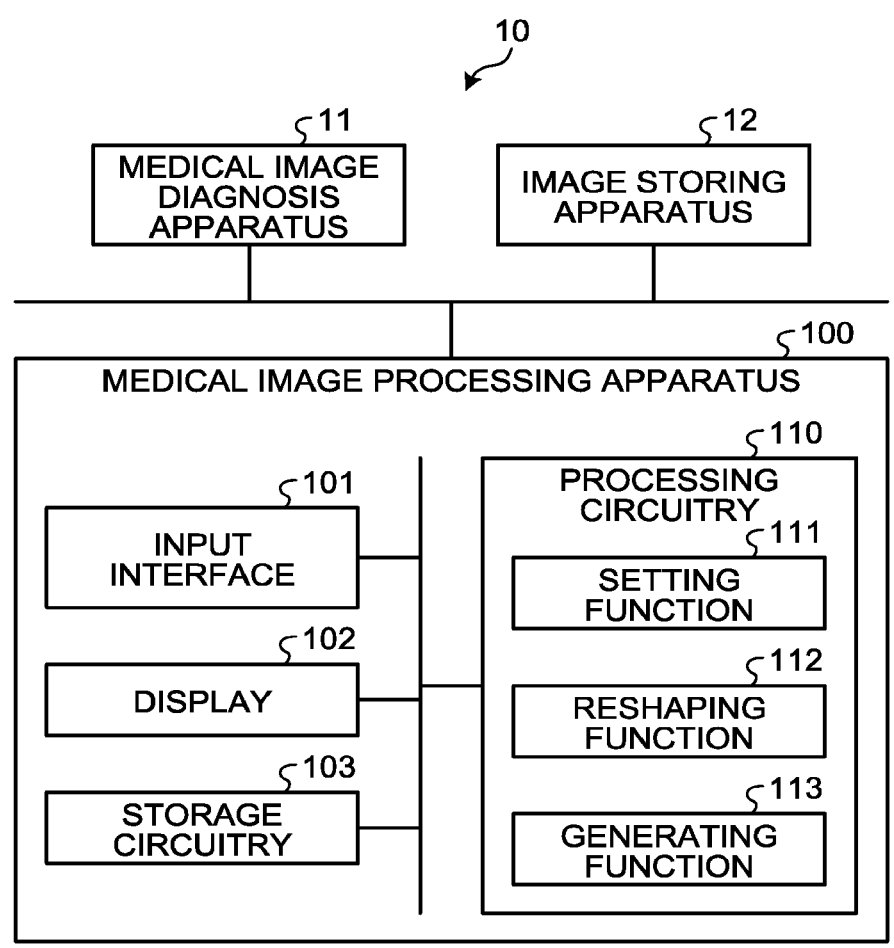
FIG. 1 is a block diagram illustrating an exemplary configuration of a medical image processing system according to an embodiment.

FIG. 1 is a block diagram illustrating an exemplary configuration of a medical image processing system according to an embodiment. As illustrated in FIG. 1, for example, a medical image processing system 10 according to the embodiment includes a medical image diagnosis apparatus 11, an image storing apparatus 12, and a medical image processing apparatus 100. The medical image diagnosis apparatus 11, the image storing apparatus 12, and the medical image processing apparatus 100 are communicably connected to one another via a network. It is possible to arbitrarily change the location where the medical image diagnosis apparatus 11, the image storing apparatus 12, and the medical image processing apparatus 100 are installed as long as the connection via the network is possible. For example, the medical image processing apparatus 100 may be installed in a facility (a hospital) different from the one in which the medical image diagnosis apparatus 11 is installed.

The medical image diagnosis apparatus 11 is an apparatus configured to take medical image data. The medical image diagnosis apparatus 11 is configured to take the medical image data depicting the inside of the body of an examined subject (hereinafter, "patient") P and to transmit the taken medical image data to either the image storing apparatus 12 or the medical image processing apparatus 100.

In the embodiments described below, an example will be explained in which an X-ray Computed Tomography (CT) apparatus is used as the medical image diagnosis apparatus 11; however, possible embodiments are not limited to this example. For instance, as the medical image diagnosis apparatus 11, it is possible to use any of the following: an X-ray diagnosis apparatus, a Magnetic Resonance Imaging (MRI) apparatus, a Single Photon Emission Computed Tomography (SPECT) apparatus, a Positron Emission computed Tomography (PET) apparatus, a SPECT-CT apparatus in which a SPECT apparatus and an X-ray CT apparatus are integrally formed, a PET-CT apparatus in which a PET apparatus and an X-ray CT apparatus are integrally formed, and a group made up of any of these apparatuses.

The image storing apparatus 12 is an apparatus configured to store therein the medical image data taken by the medical image diagnosis apparatus 11. The image storing apparatus 12 is configured to obtain the medical image data from the medical image diagnosis apparatus 11 via a network and to store the obtained medical image data into a memory provided inside or outside the apparatus. For example, the image storing apparatus 12 is realized by using a computer device such as a server apparatus.

The medical image processing apparatus 100 is configured to obtain the medical image data via the network and to perform various types of processes by using the obtained medical image data. For example, the medical image processing apparatus 100 obtains the medical image data from either the medical image diagnosis apparatus 11 or the image storing apparatus 12 via the network. Further, the medical image processing apparatus 100 is configured to execute processing functions to enhance browsability of joints, by using the obtained medical image data. For example, the medical image processing apparatus 100 is realized by using a computer device such as a workstation.

As illustrated in FIG. 1, the medical image processing apparatus 100 includes an input interface 101, a display 102, storage circuitry 103, and processing circuitry 110. The input interface 101, the display 102, the storage circuitry 103, and the processing circuitry 110 are connected to one another.

The input interface 101 is configured to receive various types of input operations from an operator, to convert the received input operations into electrical signals, and to output the electrical signals to the processing circuitry 110. For example, the input interface 101 is realized by using a mouse, a keyboard, a trackball, a switch, a button, a joystick, a touchpad on which input operations are performed by touching an operation surface thereof, a touch screen in which a display screen and a touchpad are integrally formed, contactless input circuitry using an optical sensor, audio input circuitry, and/or the like. Alternatively, the input interface 101 may be configured by using a tablet terminal or the like capable of wirelessly communicating with the main body of the medical image processing apparatus 100. Further, the input interface 101 does not necessarily have to include physical operation component parts such as a mouse, a keyboard, and/or the like. Possible examples of the input interface 101 include electrical signal processing circuitry configured, for example, to receive electrical signals corresponding to input operations from an external input device provided separately from the medical image processing apparatus 100 and to output the received electrical signals to the processing circuitry 110.

The display 102 is configured to display various types of information. For example, under control of the processing circuitry 110, the display 102 is configured to display a reshaped region specified by the processing circuitry 110 and a fluid index calculated by the processing circuitry 110. Further, the display 102 is configured to display a Graphical User Interface (GUI) used for receiving various types of instructions and various types of settings from the operator via the input interface 101. For example, the display 102 may be a liquid crystal display device or a Cathode Ray Tube (CRT) display device. The display 102 may be of a desktop type or may be configured by using a tablet terminal or the like capable of wirelessly communicating with the main body of the medical image processing apparatus 100.

For example, the storage circuitry 103 is realized by using a semiconductor memory element such as a Random Access Memory (RAM) or a flash memory, or a hard disk, an optical disk, or the like. For example, the storage circuitry 103 is configured to store therein the medical image data obtained from either the medical image diagnosis apparatus 11 or the image storing apparatus 12. Further, for example, the storage circuitry 103 is configured to store therein one or more programs for enabling the circuitry included in the medical image processing apparatus 100 to realize the functions thereof.

The processing circuitry 110 is configured to control entire processes performed by the medical image processing apparatus 100. For example, as illustrated in FIG. 1, the processing circuitry 110 is configured to execute a setting function 111, a reshaping function 112, and a generating function 113. In the present example, the setting function 111 is an example of a setting unit. The reshaping function 112 is an example of a reshaping unit. The generating function 113 is an example of a generating unit.

In this situation, for example, processing functions executed by the constituent elements of the processing circuitry 110 illustrated in FIG. 1, namely, the setting function 111, the reshaping function 112, and the generating function 113, are recorded in the storage circuitry 103 in the form of computer-executable programs. The processing circuitry 110 is a processor configured to realize the functions corresponding to the programs by reading and executing the programs from the storage circuitry 103. In other words, the processing circuitry 110 that has read the programs has the functions illustrated within the processing circuitry 110 in FIG. 1.

In the present embodiments, an example will be explained in which the single piece of processing circuitry (the processing circuitry 110) realizes the processing functions described below. However, it is also acceptable to structure processing circuitry by combining together a plurality of independent processors, so that the functions are realized as a result of the processors executing the programs.

The term "processor" used in the above explanations denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in storage circuitry. Alternatively, instead of saving the programs in the storage circuitry 103, it is also acceptable to directly incorporate the programs into the circuitry of the one or more processors. In that situation, the one or more processors realize the functions by reading and executing the programs incorporated in the circuitry thereof. Further, the processors of the present embodiments do not each necessarily have to be configured as a single piece of circuitry. It is also acceptable to structure one processor by combining together two or more pieces of independent circuitry so as to realize the functions thereof. Further, two or more of the constituent elements illustrated in the drawings may be integrated into one processor so as to realize the functions thereof.

Figure 2:
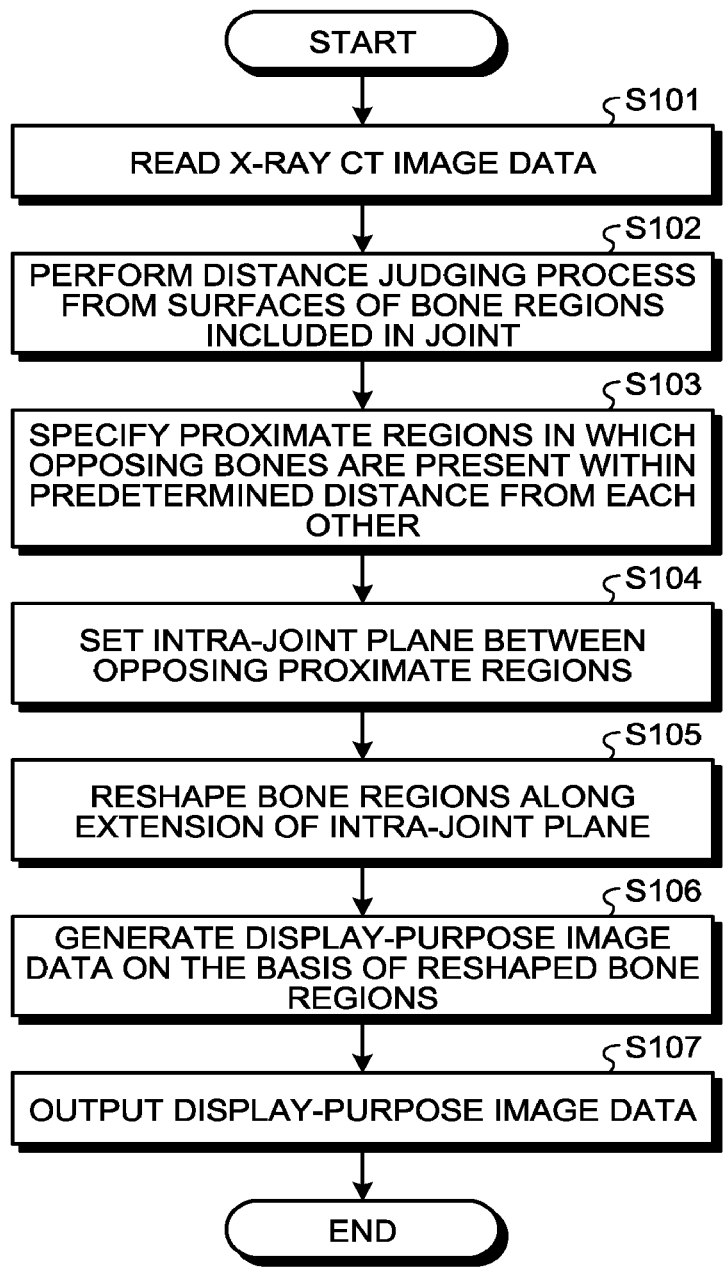
FIG. 2 is a flowchart illustrating a processing procedure performed by a medical image processing apparatus according to the embodiment.

FIG. 2 is a flowchart illustrating a processing procedure performed by the medical image processing apparatus 100 according to the embodiment. The processing procedure illustrated in FIG. 2 is started when the operator inputs an instruction indicating that a joint analysis be started.

As illustrated in FIG. 2, the processing circuitry 110 reads X-ray CT image data (step S101). For example, the processing circuitry 110 reads, from the storage circuitry 103, the X-ray CT image data stored while being kept in correspondence with identification information of the patient subject to the analysis.

In this situation, the X-ray CT image data according to the present embodiment is three-dimensional medical image data obtained by imaging a region (a site) including a joint of the patient subject to the analysis. The X-ray CT image data is basically stored in the storage circuitry 103 in advance; however, when the X-ray CT image data is not stored, the processing circuitry 110 is capable of obtaining the X-ray CT image data from either the medical image diagnosis apparatus 11 or the image storing apparatus 12.

In the following sections, an example will be explained in which the image data subject to the analysis is X-ray CT image data at a point in time; however, possible embodiments are not limited to this example. For instance, the image data subject to the analysis may be X-ray CT image data in a time series (which may be referred to as "four-dimensional X-ray CT image data" or "4D CT image data") obtained by imaging movements of the joint such as flexion and extension while performing a dynamic scan. In another example, the image data subject to the analysis may be two or more pieces of X-ray CT image data obtained by imaging mutually the same site (mutually the same joint) in (at) two or more mutually-different temporal phases (times) such as before and after treatment. In that situation, processes according to the present embodiments are performed on each of the pieces of X-ray CT image data taken in the mutually-different temporal phases.

Further, the image data subject to the analysis does not necessarily have to be X-ray CT image data and may be image data taken by other types of medical image diagnosis apparatuses, such as Magnetic Resonance (MR) image data, for example.

Subsequently, the setting function 111 performs a distance judging process from the surfaces of the bone regions included in the joint (step S102). In this situation, for example, the distance judging process is a process (a hit-test) to judge whether or not a bone region opposing a certain bone region is present within a predetermined distance.

Figure 3:
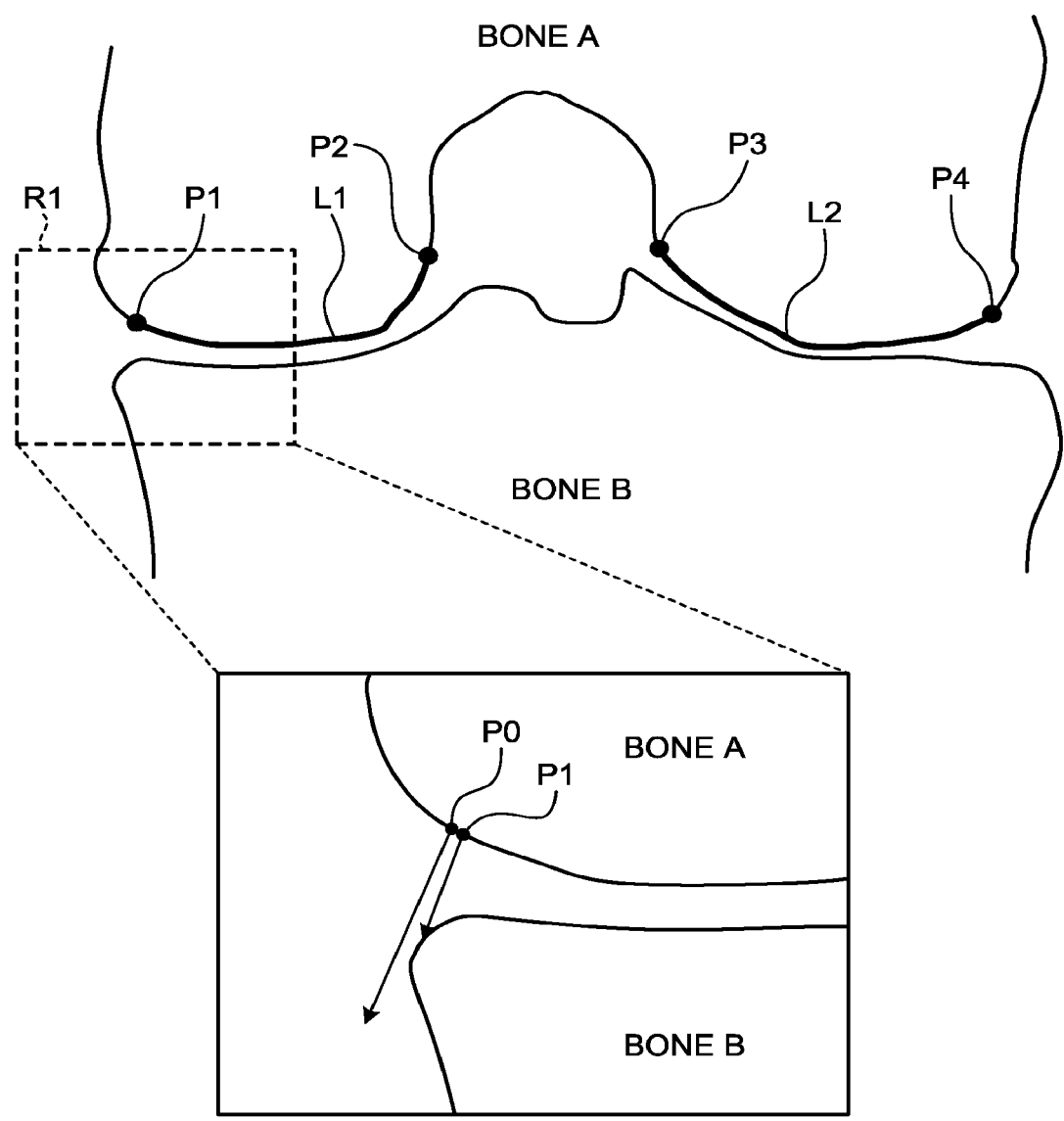
FIG. 3 is a drawing for explaining a process performed by a setting function according to the embodiment.
Figure 4:
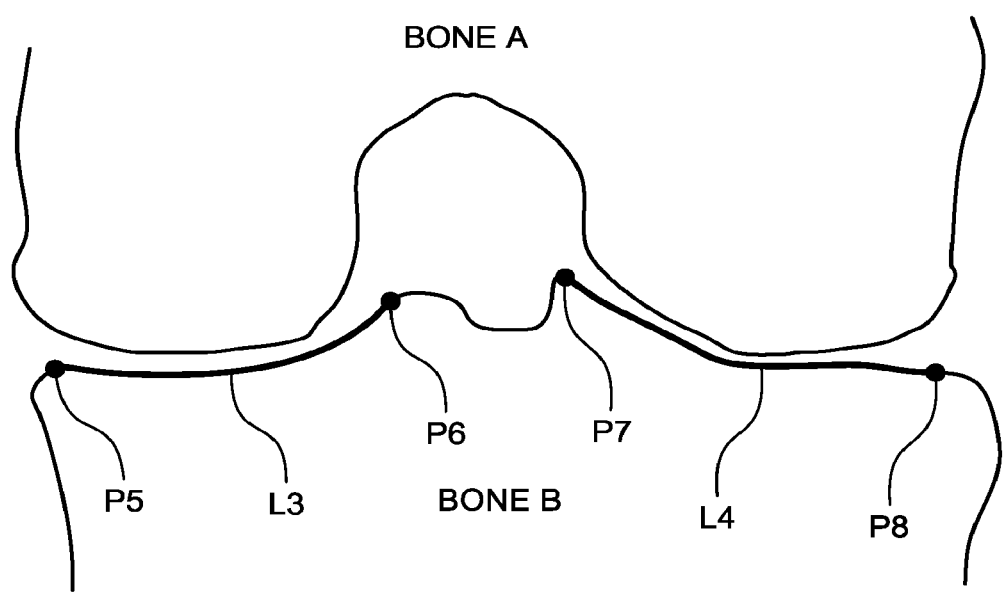
FIG. 4 is another drawing for explaining the process performed by the setting function according to the embodiment.

FIGS. 3 and 4 are drawings for explaining a process performed by the setting function 111 according to the embodiment. To explain, FIGS. 3 and 4 use cross-sectional views represented by X-ray CT image data depicting a knee joint. The cross-sectional views each correspond to a view of the knee joint taken from the front of the patient. Further, the bone A corresponds to a femur, whereas the bone B corresponds to a tibia. Also, FIG. 3 includes an enlarged view of the region R1.

As illustrated in FIG. 3, the setting function 111 performs the distance judging process to specify a point at which the region of the bone B is present within a predetermined distance from each of the points (voxels) on the surface (the contour) of the region of the bone A. In one example, the setting function 111 draws a line perpendicular to the surface from each of the points on the surface (the contour) of the region of the bone A. Further, the setting function 111 extends the drawn perpendicular lines toward the region of the bone B and specifies the points intersecting the region of the bone B within the predetermined distance. In this situation, the "predetermined distance" is set as a distance value indicating a possibility that the opposing bones may collide with each other.

More specifically, as illustrated in the enlarged view in FIG. 3, the setting function 111 draws a perpendicular line from each of the points P0 and P1 toward the bone B. In this situation, the perpendicular line drawn from the point P0 does not intersect the region of the bone B, whereas the perpendicular line drawn from the point P1 intersects the region of the bone B within the predetermined distance. In this situation, the setting function 111 specifies the point P1.

With respect to the other points on the surface of the region of the bone A, the setting function 111 similarly performs the distance judging process. As a result, as illustrated in FIG. 3, the setting function 111 specifies a curve L1 connecting the point P1 to another point P2, as well as another curve L2 connecting a point P3 to another point P4.

Further, with respect to each of the points on the surface of the region of the bone B, the setting function 111 performs the distance judging process. As a result, as illustrated in FIG. 4, the setting function 111 specifies a curve L3 connecting a point P5 to another point P6, as well as another curve L4 connecting a point P7 to another point P8.

In FIGS. 3 and 4, because the cross-sectional views are illustrated, the example in which the curves L1, L2, L3, and L4 are specified was explained; however, in the three-dimensional medical image data, each of the "curves" is specified as a "curved plane".

Further, FIGS. 3 and 4 illustrate the examples in which the perpendicular lines intersect the opposing bone region; however, there may be other situations where a perpendicular line intersects the originating bone region. As a specific example, a perpendicular line drawn from the surface of the bone A may intersect the region of the bone A. This situation does not correspond to an "opposing bone", but is conjectured to be a recess or a crack on the surface of the bone A. Accordingly, the setting function 111 is configured not to specify points intersecting the originating bone region.

The configurations explained with reference to FIGS. 3 and 4 are merely examples, and possible embodiments are not limited to the above description. For instance, in the above explanations, the example was explained in which the line perpendicular to the surface (the perpendicular line) is drawn from each of the points on the surface of each of the bones, so as to measure the distance (i.e., the distance in the direction of the perpendicular line) to the intersection with the opposing bone region; however, possible embodiments are not limited to this example. In another example, the setting function 111 may use a central line of the entire region of the bone A (the extending direction of the femur) as a reference direction, so as to draw a line along the reference direction and to measure the distance (i.e., the distance in the direction of the central line) to the intersection with the region of the bone B.

Returning to the description of FIG. 2, the setting function 111 specifies proximate regions in which opposing bones are present within a predetermined distance from each other (step S103). For example, the setting function 111 specifies regions in which the curve L1 and the curve L3 are present within the predetermined distance from each other.

Figure 5:
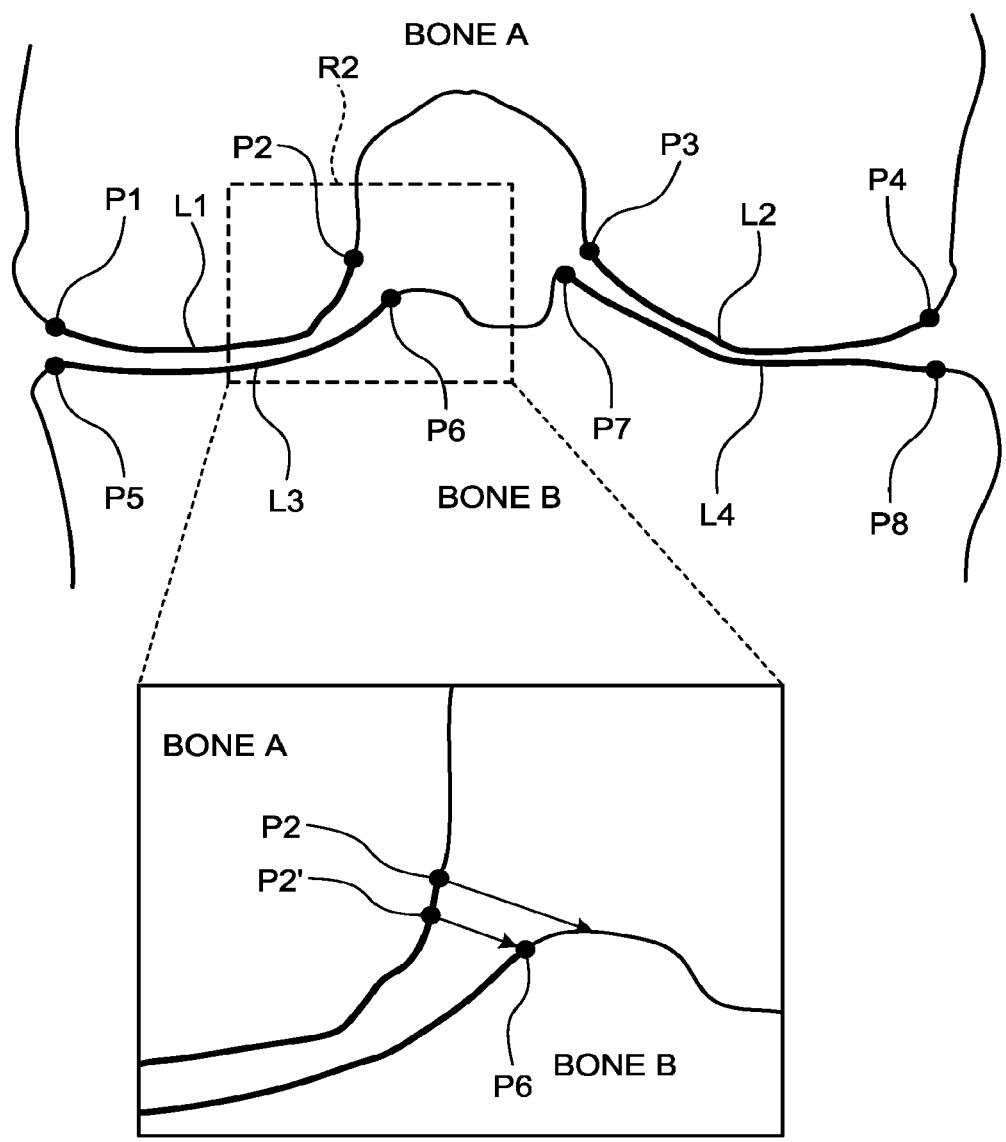
FIG. 5 is a drawing for explaining another process performed by the setting function according to the embodiment.
Figure 6:
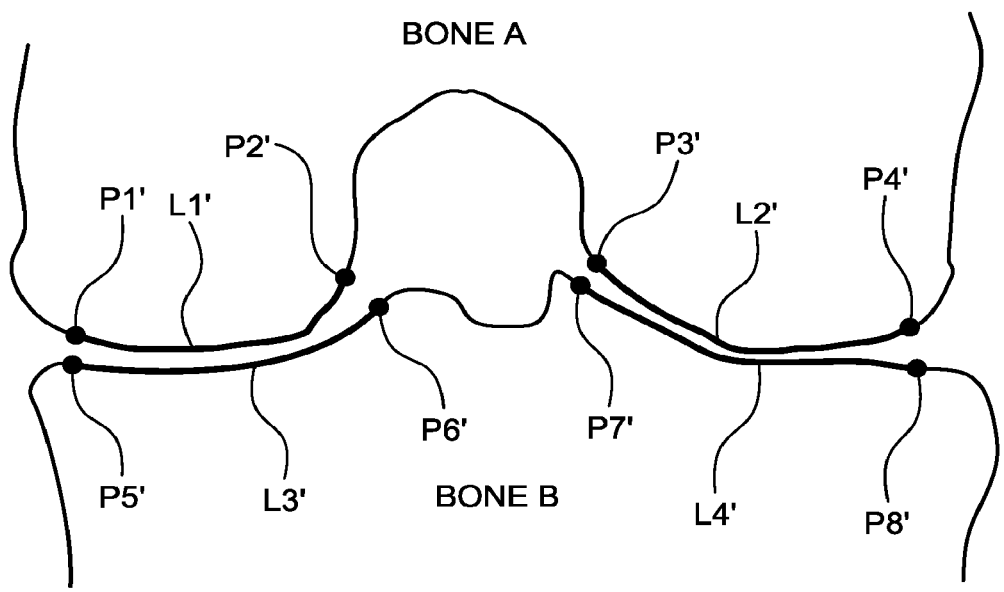
FIG. 6 is another drawing for explaining said another process performed by the setting function according to the embodiment.

FIGS. 5 and 6 are drawings for explaining another process performed by the setting function 111 according to the embodiment. To explain, FIGS. 5 and 6 use cross-sectional views similar to those in FIGS. 3 and 4. Further, FIG. 5 includes an enlarged view of the region R2.

As illustrated in FIG. 5, for example, the setting function 111 specifies a region including such points among the points on the curve L1 from which drawn perpendicular lines intersect the curve L3, as a proximate region. As illustrated in the enlarged view in FIG. 5, the setting function 111 draws a perpendicular from each of the points P2 and P2' toward the bone B. In this situation, the perpendicular line drawn from the point P2 intersects the region of the bone B, but does not intersect the curve L3. In contrast, the perpendicular line drawn from the point P2' intersects the curve L3. Accordingly, of the curve L1, the points from the point P2 to the point P2' have the possibility of not colliding with the opposing bone in actuality. Consequently, of the curve L1, the setting function 111 specifies the point P2' that can cause an intersection with the curve L3 and excludes the points from the point P2 to the point P2'.

Similarly, with respect to the other points on the curve L1, the setting function 111 specifies points that can each cause an intersection with the curve L3. As a result, as illustrated in FIG. 6, the setting function 111 specifies, of the curve L1, a curve L1' that can cause intersections with the curve L3. The curve L1' (the curve connecting a point P1' to the point P2') corresponds to a proximate region.

Similarly, with respect to each of the curves L2, L3, and L4, the setting function 111 specifies a curve that can cause intersections with the opposing curve. More specifically, of the curve L2, the setting function 111 specifies a curve L2' (the curve connecting a point P3' to another point P4') that can cause intersections with the curve L4. Further, of the curve L3, the setting function 111 specifies a curve L3' (the curve connecting a point P5' to another point P6') that can cause intersections with the curve L1. Also, of the curve L4, the setting function 111 specifies a curve L4' (the curve connecting a point P7' to another point P8') that can cause intersections with the curve L2. The curves L2', L3', and L4' each correspond to a proximate region. In this situation, in the three-dimensional medical image data, each of the curves L1', L2', L3', and L4' is specified as a "curved plane".

As explained above, among the bone regions included in the joint, the setting function 111 specifies the proximate regions each of which is present within the predetermined distance from another proximate region.

Returning to the description of FIG. 2, the setting function 111 sets an intra-joint plane between the opposing proximate regions (step S104). For example, the setting function 111 sets the intra-joint plane in the middle of the proximate regions of the bone regions. The intra-joint plane is an example of the "curved plane" between the first bone region and the second bone region included in the joint.

Figure 7:
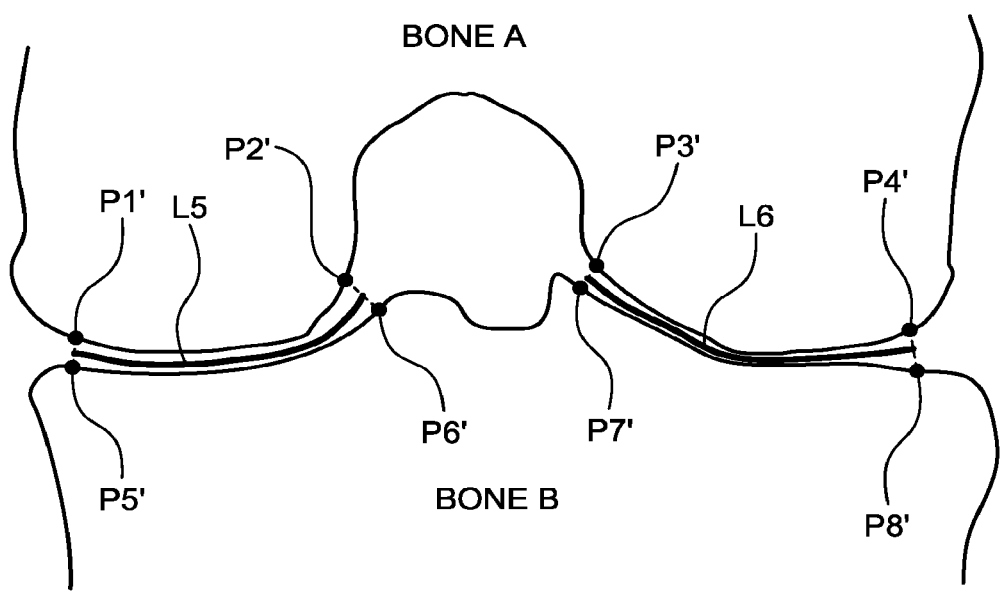
FIG. 7 is a drawing for explaining yet another process performed by the setting function according to the embodiment.

FIG. 7 is a drawing for explaining yet another process performed by the setting function 111 according to the embodiment. To explain, FIG. 7 uses a cross-sectional view similar to those in FIGS. 3 to 6.

As illustrated in FIG. 7, with respect to each of the points on the curve L1', the setting function 111 specifies a line segment representing the shortest distance to the opposing curve L3'. Further, by connecting together the middle points of the specified line segments, the setting function 111 sets a curve L5. The curve L5 passes through the middle point of the line segment connecting the point P1' to the point P5' and the middle point of the line segment connecting the point P2' to the point P6'. In other words, the curve L5 corresponds to the "intra-joint plane" between the curve L1' and the curve L3'.

Similarly, with respect to the curve L2' and the curve L4', the setting function 111 sets a curve L6 as an intra-joint plane between the two curves. In the three-dimensional medical image data, each of the curves L5 and L6 is set as a "curved plane".

As explained above, in the three-dimensional medical image data obtained by imaging the joint including at least the first bone region and the second bone region, the setting function 111 is configured to set the curved plane between the first bone region and the second bone region included in the joint. The configuration explained with reference to FIG. 7 is merely an example, and possible embodiments are not limited to the above description. For example, the intra-joint plane is not limited to the plane passing through the middle points of the line segments each representing the shortest distance between the opposing proximate regions. For instance, the setting function 111 may draw perpendicular lines from one of the two opposing bone regions to the other, so as to set a plane passing through the middle points of the perpendicular lines as an intra-joint plane. Further, it is not necessary to use the "middle points", and points deviated from the middle points may be used, as long as no impact is made on the processing.

Returning to the discerption of FIG. 2, the reshaping function 112 reshapes the bone regions, along extension of the intra-joint plane (step S105). For example, the reshaping function 112 reshapes the proximate regions along the extension of the curved plane (the intra-joint plane), but does not reshape the regions other than the proximate regions.

Figure 8:
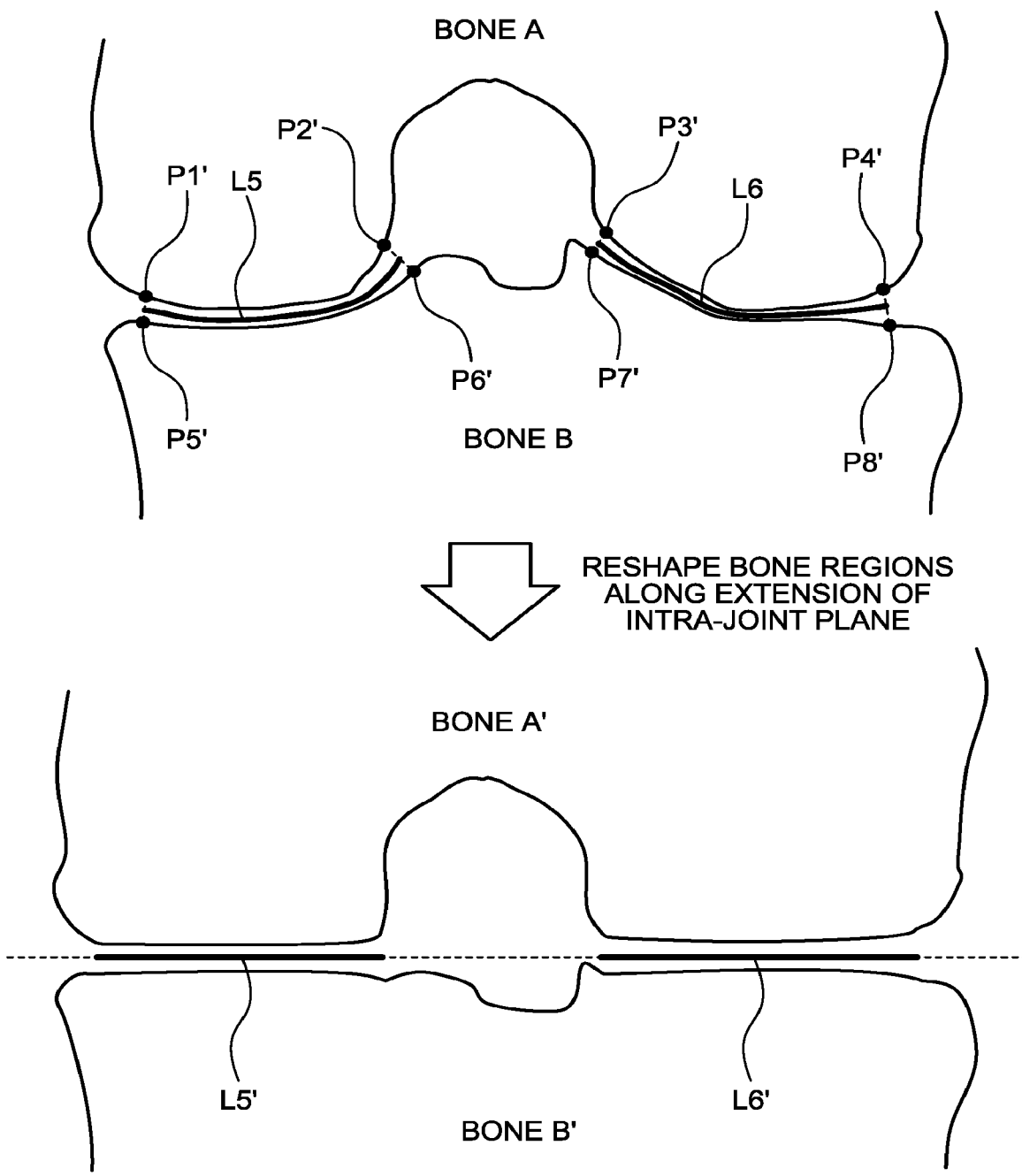
FIG. 8 is a drawing for explaining a process performed by a reshaping function according to the embodiment.

FIG. 8 is a drawing for explaining a process performed by the reshaping function 112 according to the embodiment. To explain, FIG. 7 uses cross-sectional views similar to those in FIGS. 3 to 7. Similarly to FIG. 7, the top section of FIG. 8 illustrates a cross-sectional view prior to a reshaping process performed by the reshaping function 112. The bottom section of FIG. 8 illustrates a cross-sectional view after the reshaping process performed by the reshaping function 112.

As illustrated in FIG. 8, the reshaping function 112 is configured to extend the curves L5 and L6 on mutually the same flat plane. As a result, as illustrated in the bottom section of FIG. 8, the reshaping function 112 generates a straight line L5' and another straight line L6'. In this situation, to the process of extending the curves L5 and L6, it is possible to arbitrarily apply a publicly-known technique, such as a technique for reshaping (stretching or contracting) the curve to be a straight line or a technique for projecting the curve onto a flat plane so as to be reshaped as a straight line, for example.

Further, along the extension of the curve L5 to become the straight line L5', the reshaping function 112 reshapes each of the curves L1' and L3'. For example, the reshaping function 112 defines a ratio of the change from the curve L5 to the straight line L5' and further reshapes each of the curves L1' and L3' on the basis of the defined ratio. As a result, as illustrated in the bottom section of FIG. 8, the reshaping function 112 reshapes each of the curves L1' and L3' along the extension of the curve L5.

Further, along the extension of the curve L6 to become the straight line L6', the reshaping function 112 reshapes each of the curves L2' and L4'. For example, the reshaping function 112 defines a ratio of the change from the curve L6 to the straight line L6' and further reshapes each of the curves L2' and L4' on the basis of the defined ratio. As a result, as illustrated in the bottom section of FIG. 8, the reshaping function 112 reshapes each of the curves L2' and L4' along the extension of the curve L6.

Further, in the regions of the bone A and bone B, the reshaping function 112 does not reshape the regions other than the proximate regions. Accordingly, for example, the reshaping function 112 maintains the shape formed between the curve L1' and the curve L2' and the shape formed between the curve L3' and the curve L4'. As a result, of the bones A and B, the reshaping function 112 reshapes the proximate regions while keeping the original structure of the parts other than the proximate regions. Accordingly, although the proximate regions are planarly reshaped, the original structures of the parts (e.g., the recess) other than the proximate regions remain. The operator is therefore able to easily understand the correspondence relationship with the original structures.

In this manner, along the extension of the intra-joint plane, the reshaping function 112 reshapes the first bone region and the second bone region to obtain the reshaped bone regions. For example, as illustrated in the bottom section of FIG. 8, the reshaping function 112 obtains, as the reshaped bone regions, two bone regions that are, namely, a region of the bone A including the curve L1' and the curve L2' resulting from the reshaping, as well as a region of the bone B including the curve L3' and the curve L4' resulting from the reshaping.

The configuration explained with reference to FIG. 8 is merely an example, and possible embodiments are not limited to the above description. For instance, the example was explained with reference to FIG. 8 in which the regions that are not to be reshaped (i.e., the regions other than the proximate regions) are automatically determined; however, possible embodiments are not limited to this example. For instance, the reshaping function 112 may be configured so as not to reshape a region designated by the operator. In other words, the reshaping function 112 may be configured to receive an input operation from the operator designating an arbitrary region in the first and the second bone regions and to reshape the region other than the designating region, without reshaping the designating region.

Further, the reshaping function 112 does not necessarily have to reshape all the bones included in the joint. For example, among the plurality of bones included in the joint, the reshaping function 112 may reshape only a bone subject to the analysis. In other words, the reshaping function 112 is configured to reshape at least one of the first and the second bone regions, along the extension of the intra-joint plane.

With reference to FIG. 8, the example was explained in which the bone regions are reshaped along the extension of the intra-joint plane; however, possible embodiments are not limited to this example. For instance, instead of reshaping only the bone regions included in the medical image data (volume data), the reshaping function 112 may reshape the entire medical image data on the basis of the curve (the extension) of the curved plane.

Further, for example, instead of reshaping the medical image data itself being input as the data subject to the analysis, the reshaping function 112 may create a copy of the medical image data for the purpose of a curved plane mapping calculation, so as to reshape the medical image data in the created copy version.

Further, for example, instead of reshaping the medical image data, the reshaping function 112 may be configured to reshape coordinate axes indicating voxel positions in the medical image data. In other words, the reshaping function 112 may be configured to calculate, in advance, a list of reference coordinates defining at which coordinates the values in the original volume data should be referenced when mapping a parameter on the curved plane. Further, according to the list of the reference coordinates, by referencing the values in the volume data that has not been reshaped, the reshaping function 112 is able to determine the values to be mapped onto the curved plane.

Returning to the description of FIG. 2, the generating function 113 generates display-purpose image data on the basis of the bone regions resulting from the reshaping (step S106).

Figure 9:
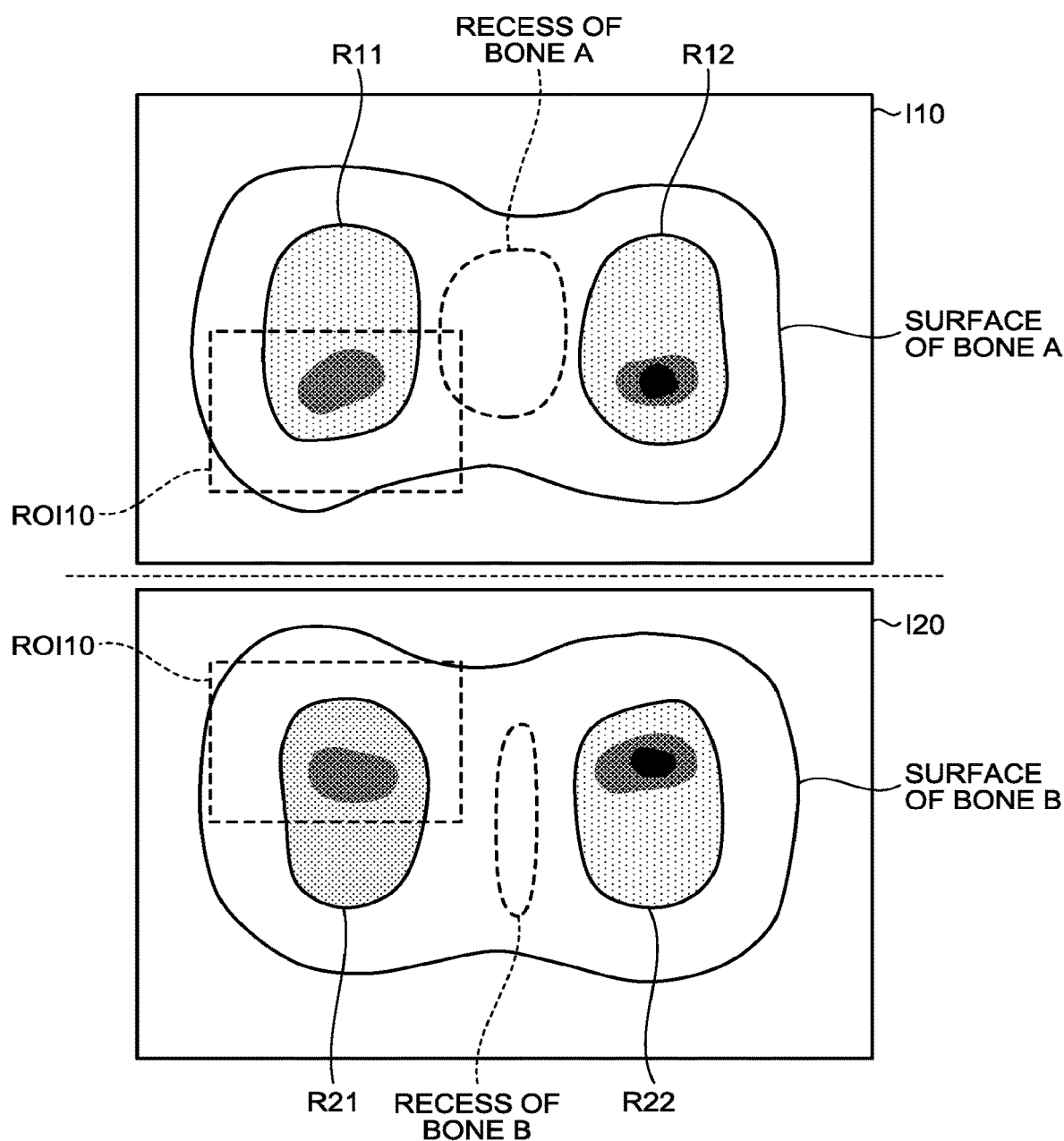
FIG. 9 is a drawing for explaining a process performed by a generating function according to the embodiment.

FIG. 9 is a drawing for explaining a process performed by the generating function 113 according to the embodiment. The top section of FIG. 9 illustrates a rendering image of the surface of the caput of a bone A' (a femur) viewed from the side of a bone B' (the tibia side). Further, the bottom section of FIG. 9 illustrates a rendering image of the surface of the caput of the bone B' (the tibia) viewed from the side of the bone A' (the femur side). It is desirable to collectively display the images in the top and the bottom sections of FIG. 9, in the positional arrangement as illustrated.

As illustrated in FIG. 9, for example, the generating function 113 generates an image I10 that is the rendering image of the surface of the caput of the bone A', by performing a surface rendering process on image data of the reshaped bone A' illustrated in FIG. 8. The image I10 depicts a region R11 corresponding to the proximate region including the curve L1', a region R12 corresponding to the proximate region including the curve L2', the recess of the bone A', and the like. Because the recess of the bone A' has not been reshaped by the reshaping function 112, the recess is useful in understanding the correspondence relationship with the original structure of the bone A before the reshaping.

Further, the generating function 113 maps index values indicating the degrees of bone intervals onto the region R11 and the region R12. For example, each of the index values indicates the distance (e.g., the distance in the direction of a perpendicular line) to the surface of the opposing bone. In other words, to each of the points in the regions R11 and R12, a pixel value corresponding to the distance to a point of the bone B' opposing the point is assigned. In this manner, as the display-purpose image data, the generating function 113 generates the image data obtained by mapping the index values indicating the degrees of intervals between the first bone region and the second bone region, onto the surfaces of the reshaped bone regions. In this situation, the index values indicating the degrees of the bone intervals are examples of the first index value.

Similarly to the bone A', with respect to the bone B', the generating function 113 generates an image I20 that is a rendering image of the surface of the caput of the bone B', by performing a surface rendering process on image data of the reshaped bone B' illustrated in FIG. 8. The image I20 depicts a region R21 corresponding to the proximate region including the curve L3', a region R22 corresponding to the proximate region including the curve L4', the recess of the bone B', and the like. Because the recess of the bone B' has not been reshaped by the reshaping function 112, the recess is useful in understanding the correspondence relationship with the original structure of the bone B before the reshaping.

Further, the generating function 113 maps index values indicating the degrees of bone intervals onto the region R21 and the region R22. Because the index values are the same as the index values mapped on the region R11 and the region R12, the explanations thereof will be omitted.

Further, the generating function 113 causes a region of interest ROI10 to be displayed. For example, the operator designates the position and the area (size) of the region of interest ROI10 within the image I10. The generating function 113 causes the region of interest ROI10 to be displayed in the position and the area designated by the operator. In this situation, it is possible to define, in advance, correspondence relationships between the positions of the points in the region R11 and the positions of the points in the region R21 opposing the region R11. For example, the correspondence relationships are defined as a result of extending a line perpendicular to the intra-joint plane in both directions and bringing a point in the region R11 and a point in the region R21 that intersect the perpendicular line into correspondence with each other in advance. Accordingly on the basis of the correspondence relationships, the generating function 113 identifies the positions in the image I20 corresponding to the region of interest ROI10 within the image I10. Further, the generating function 113 is also able to arrange the region of interest ROI10 into the identified position within the image I20. In other words, when the region of interest ROI10 has been set or changed in one of the images I10 and I20, the generating function 113 is able to cause the setting or the changing to be reflected in the other image.

As explained above, the generating function 113 is configured to generate the display-purpose image data on the basis of the reshaped bone regions resulting from the reshaping by the reshaping function 112. The configuration explained with reference to FIG. 8 is merely an example, and possible embodiments are not limited to the above description. For instance, in FIG. 9, the index values may be calculated on the basis of "distances in the direction of the central lines" in place of the "distances in the direction of the perpendicular lines".

Further, when the image data subject to the analysis includes pieces of image data in a plurality of temporal phases, it is also possible to calculate index values while taking the concept of time into account. For example, when the data subject to the analysis is 4D CT image data obtained by imaging movements of the joint, the generating function 113 may be configured to calculate the distances between the bone regions with respect to each of the plurality of temporal phases. After that, the generating function 113 is configured to calculate the longest distance, the shortest distance, an average distance, and/or the like of the calculated distances, as index values. Further, the generating function 113 may calculate, as index values, the length of time during which the distance between the bone regions is equal to or shorter than a threshold value in the movements. Further, when the data subject to the analysis is two pieces of X-ray CT image data corresponding to before and after treatment, the generating function 113 may be configured to calculate the difference in the bone region distances, as an index value. In other words, as the index values, the generating function 113 is capable of calculating at least one of: the distance to the surface of the opposing bone region; the longest distance between the bone regions among the plurality of temporal phases; the shortest distance between the bone regions among the plurality of temporal phases; an average distance between the bone regions among the plurality of temporal phases; the length of time during which the distance between the bone regions is equal to or shorter than the threshold value among the plurality of temporal phases; and the difference in bone region distances between mutually-different temporal phases.

Further, the index values do not necessarily have to be mapped onto the regions R11, R12, R21, and R22. In other words, with respect to the proximate regions also, the generating function 113 is capable of generating display-purpose image data depicting the surfaces of the reshaped bone regions on the basis of CT values. Further, the generating function 113 may also be configured to generate display-purpose image data depicting the surfaces of the reshaped bone regions on the basis of the CT values and to switch between whether the proximate regions on which the index values are mapped are displayed or not, in accordance with instructions from the operator.

Further, with reference to FIG. 9, the example was explained in which the index values are mapped on the rendering image of the surface of the caput; however, possible embodiments are not limited to this example. For instance, the generating function 113 may generate image data of a flat plane obtained by extending the intra-joint plane so as to map the index values on the image data of the flat plane. In other words, as the display-purpose image data, the generating function 113 may be configured to generate the image data obtained by mapping the index values on the flat plane obtained by extending the intra-joint plane.

Returning to the description of FIG. 2, the processing circuitry 110 outputs the display-purpose image data (step S107). For example, the processing circuitry 110 causes the display 102 to display the display-purpose image data generated by the generating function 113. After that, the processing circuitry 110 ends the processing procedure in FIG. 2.

The output destination of the display-purpose image data is not limited to the display 102. For example, the processing circuitry 110 may store the display-purpose image data into the storage circuitry 103 or an arbitrary storage medium. Further, the processing circuitry 110 may transmit the display-purpose image data to the image storing apparatus 12 or an external device provided on a network.

The processing procedure illustrated in FIG. 2 is merely an example, and possible embodiments are not limited to the example in the drawing. For instance, the processing procedure illustrated in FIG. 2 does not necessarily have to be executed in the order described above. It is also acceptable to modify the processing procedure as appropriate, so long as no conflict occurs in the processing.

As explained above, the medical image processing apparatus 100 according to the embodiment is configured to set the curved plane between the first bone region and the second bone region included in the joint, in the three-dimensional medical image data. Further, the medical image processing apparatus 100 is configured to reshape at least one of the first and the second bone regions along the extension of the set curved plane. In addition, on the basis of the reshaped bone region, the medical image processing apparatus 100 is configured to generate the display-purpose image data. With these arrangements, the medical image processing apparatus 100 is able to enhance browsability of the joint.

Joints structured by a plurality of bones have a complicated shape. For example, the surface of the caput of a bone is structured to curve around from the tip end toward the lateral face, which makes it difficult to observe the entirety. Further, among the bones structuring a joint, it is not easy to identify which bones collide with each other or are positioned proximate to each other. To cope with these situations, the medical image processing apparatus 100 according to the embodiment is configured to set the intra-joint plane between the bones structuring the joint and to display the surfaces of the bones that are planarly developed along the extension of the intra-joint plane. Accordingly, even when the bones structure a joint having a complicated shape, the medical image processing apparatus 100 is able to display, on a screen, the entire region where the bones are positioned proximate to each other.

First Modification Example

In the above embodiments, the example was explained in which the joint includes the two bones; however, the present embodiment is similarly applicable to an example in which three or more bones are included.

Figure 10:
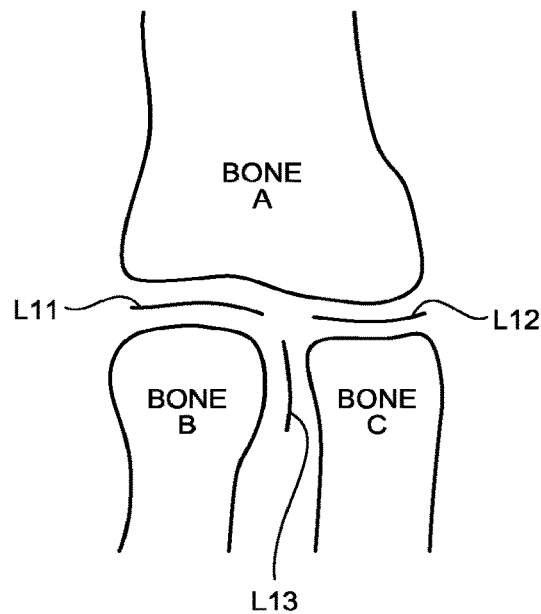
FIG. 10 is a drawing for explaining a process performed by a medical image processing apparatus according to a first modification example.
Figure 11:
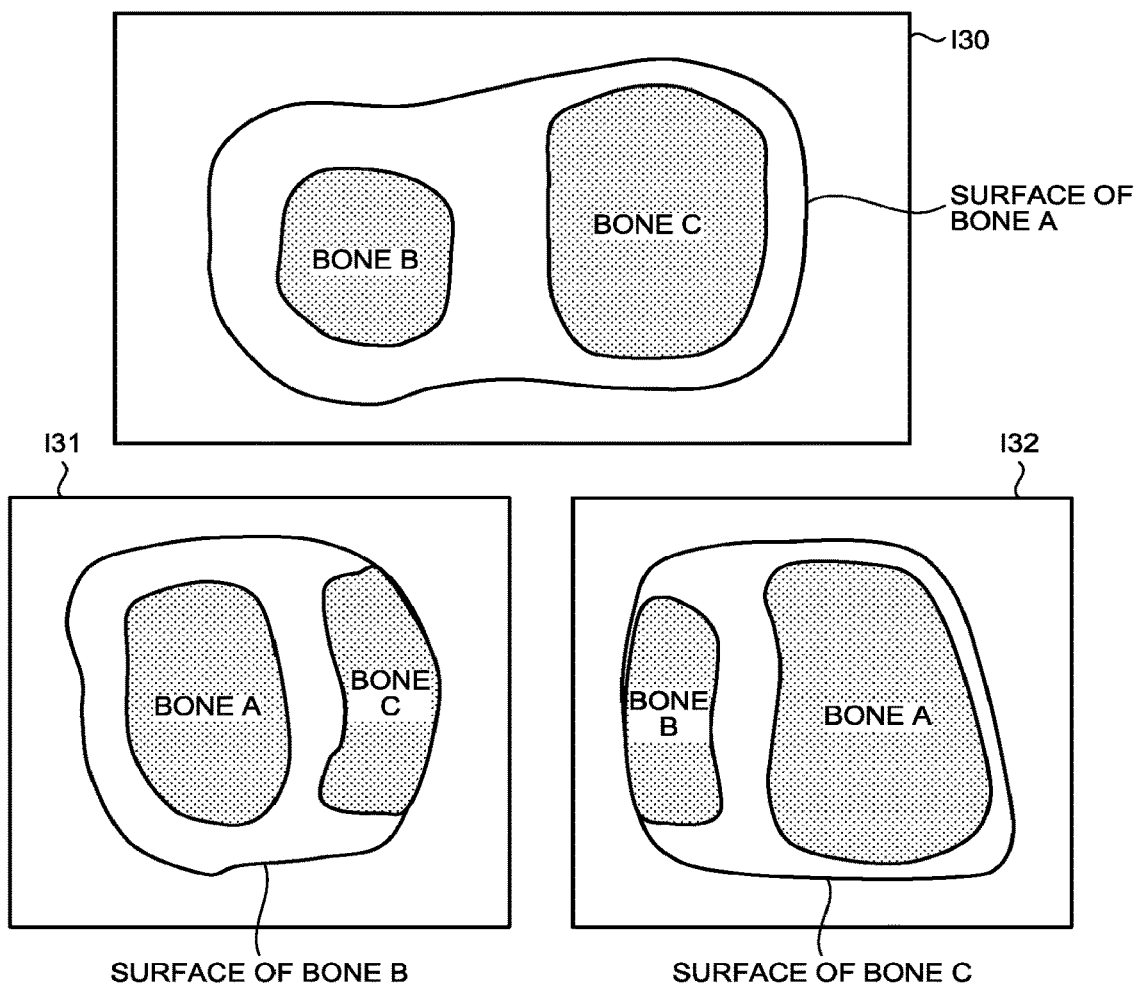
FIG. 11 is another drawing for explaining the process performed by the medical image processing apparatus according to the first modification example.

FIGS. 10 and 11 are drawings for explaining a process performed by the medical image processing apparatus 100 according to a first modification example. FIG. 10 illustrates a cross-sectional view represented by X-ray CT image data depicting an elbow joint. FIG. 11 illustrates display-purpose image data generated on the basis of the X-ray CT image data illustrated in FIG. 10. In FIGS. 10 and 11, the bone A corresponds to a humerus, while the bone B corresponds to a radius, and the bone C corresponds to an ulna.

As illustrated in FIG. 10, the setting function 111 is configured to set a curve L11 as an intra-joint plane between the bone A and the bone B. Further, the setting function 111 is configured to set a curve L12 as an intra-joint plane between the bone A and the bone C. In addition, the setting function 111 is configured to set a curve L13 as an intra-joint plane between the bone B and the bone C. Because the processes of setting the curves L11, L12, and L13 are the same as the processes of setting the curves L5 and L6, the explanations thereof will be omitted.

Further, the reshaping function 112 is configured to extend the curve L11 and the curve L12 on mutually the same flat plane. After that, the reshaping function 112 is configured to reshape the region of the bone A along the extension of the curve L11 and the curve L12. On the basis of the reshaped region of the bone A, the generating function 113 is configured to generate an image I30 as display-purpose image data (FIG. 11). In the image I30, the hatching region on the left side is a proximate region opposing the bone B, whereas the hatching region on the right side is a proximate region opposing the bone C. In this situation, in the display-purpose image data, the generating function 113 is configured to cause identification information (the labels "BONE B" and "BONE C") to be displayed for identifying the bones B and C opposing the depicted bone A.

Further, the reshaping function 112 is configured to extend the curve L11 and the curve L13 on mutually the same flat plane. After that, the reshaping function 112 is configured to reshape the region of the bone B, along the extension of the curve L11 and the curve L13. On the basis of the reshaped region of the bone B, the generating function 113 is configured to generate an image I31 as display-purpose image data (FIG. 11). Of the bone B, the image I31 depicts a proximate region "BONE A" opposing the bone A and another proximate region "BONE C" opposing the bone C.

Further, the reshaping function 112 is configured to extend the curve L12 and the curve L13 on mutually the same flat plane. Further, the reshaping function 112 is configured to reshape the region of the bone C along the extension of the curve L12 and the curve L13. On the basis of the reshaped region of the bone C, the generating function 113 is configured to generate an image I32 as display-purpose image data (FIG. 11). Of the bone C, the image I31 depicts a proximate region "BONE A" opposing the bone A and another proximate region "BONE B" opposing the bone B.

As explained above, also in the situations where three or more bones are included, the medical image processing apparatus 100 is able to enhance browsability of the joint.

Second Modification Example

Further, it is also possible to simultaneously display a plurality of bones surrounding another bone.

Figure 12:
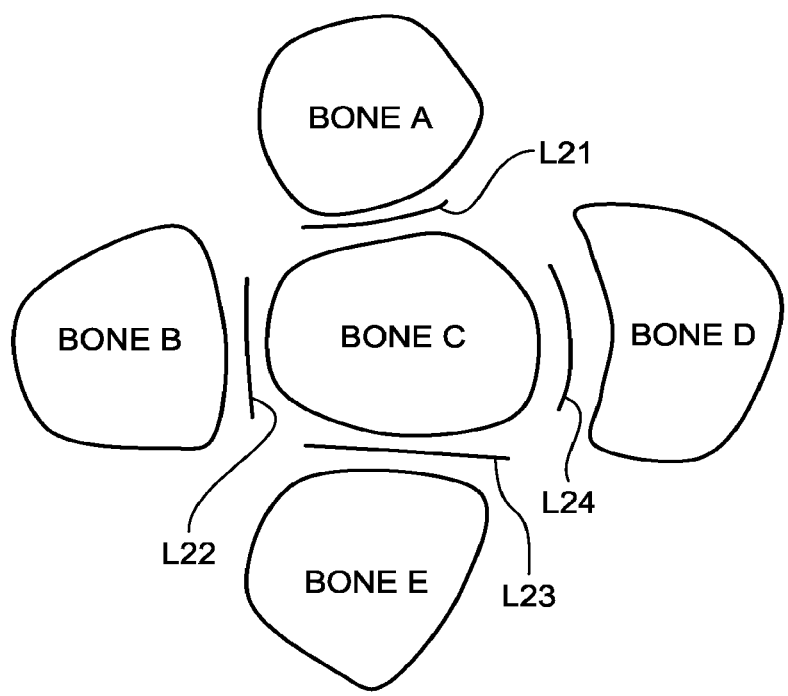
FIG. 12 is a drawing for explaining a process performed by a medical image processing apparatus according to a second modification example.
Figure 14:
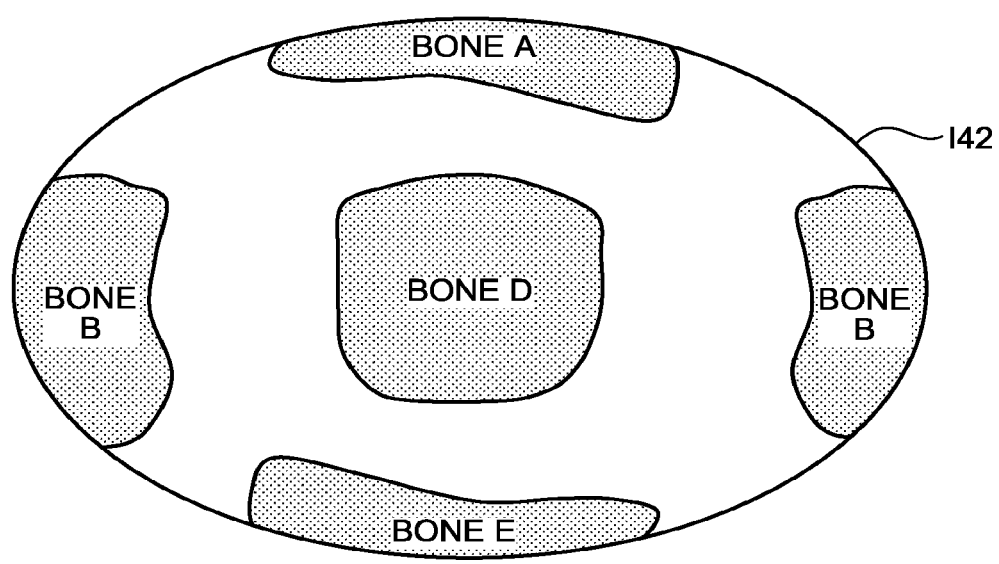
FIG. 14 is yet another drawing for explaining the process performed by the medical image processing apparatus according to the second modification example.

FIGS. 12, 13, and 14 are drawings for explaining a process performed by the medical image processing apparatus 100 according to a second modification example. FIG. 12 illustrates a cross-sectional view represented by X-ray CT image data in an example in which a region including a plurality of bones, such as the carpus, is subject to the analysis. FIGS. 13 and 14 each illustrate display-purpose image data generated on the basis of the X-ray CT image data illustrated in FIG. 12.

As illustrated in FIG. 12, the setting function 111 is configured to set a curve L21 as an intra-joint plane between the bone A and the bone C. Further, the setting function 111 is configured to set a curve L22 as an intra-joint plane between the bone B and the bone C. Also, the setting function 111 is configured to set a curve L23 as an intra-joint plane between the bone C and the bone E. In addition, the setting function 111 is configured to set a curve L24 as an intra-joint plane between the bone C and the bone D. Because the processes of setting the curves L21, L22, L23, and L24 are the same as the processes of setting the curves L5 and L6, the explanations thereof will be omitted.

Further, the reshaping function 112 is configured to extend the curve L21, the curve L22, the curve L23, and the curve L24 on mutually the same flat plane. More specifically, for example, the reshaping function 112 is configured to set a spherical plane (a deformed sphere) passing through the curves L21, L22, L23, and L24. After that, by implementing a conformal cylindrical projection method, the reshaping function 112 is configured to extend the set spherical plane to become a flat plane. As a result, the generating function 113 generates an image I40 illustrated in the top section of FIG. 13. The image I40 is an image developed by projecting the spherical plane passing through the curves L21, L22, L23, and L24 onto a cylinder and subsequently cutting open the region between the bone B and the bone C.

In this situation, the generating function 113 is configured to re-generate display-purpose image data in accordance with a scroll operation performed by the operator. For example, when a downward scroll operation is performed on the image I40, the generating function 113 generates an image I41 by moving the image I40 downward (the bottom section of FIG. 13). The generating function 113 is capable of re-generating display-purpose image data in response to scroll operations in arbitrary directions such as up-and-down directions and left-and-right directions.

The reshaping function 112 does not necessarily have to Implement the conformal cylindrical projection method and may extend the curves by implementing an equal-area projection method, for example. As a result, as display-purpose image data, the generating function 113 generates an image I42 illustrated in FIG. 14. It is also possible to receive scroll operations on the image I42.

As explained above, the medical image processing apparatus 100 is configured to simultaneously display the plurality of bones surrounding the other bone. With this arrangement, the operator is, for example, able to easily browse the status of the bones surrounding the bone C while being centered on the bone C.

Third Modification Example

Further, when the image data subject to the analysis includes pieces of image data in a plurality of temporal phases, the medical image processing apparatus 100 is capable of generating a piece of display-purpose image data in each of the plurality of temporal phases and also generating image data integrating the pieces of display-purpose image data together.

Figure 15:
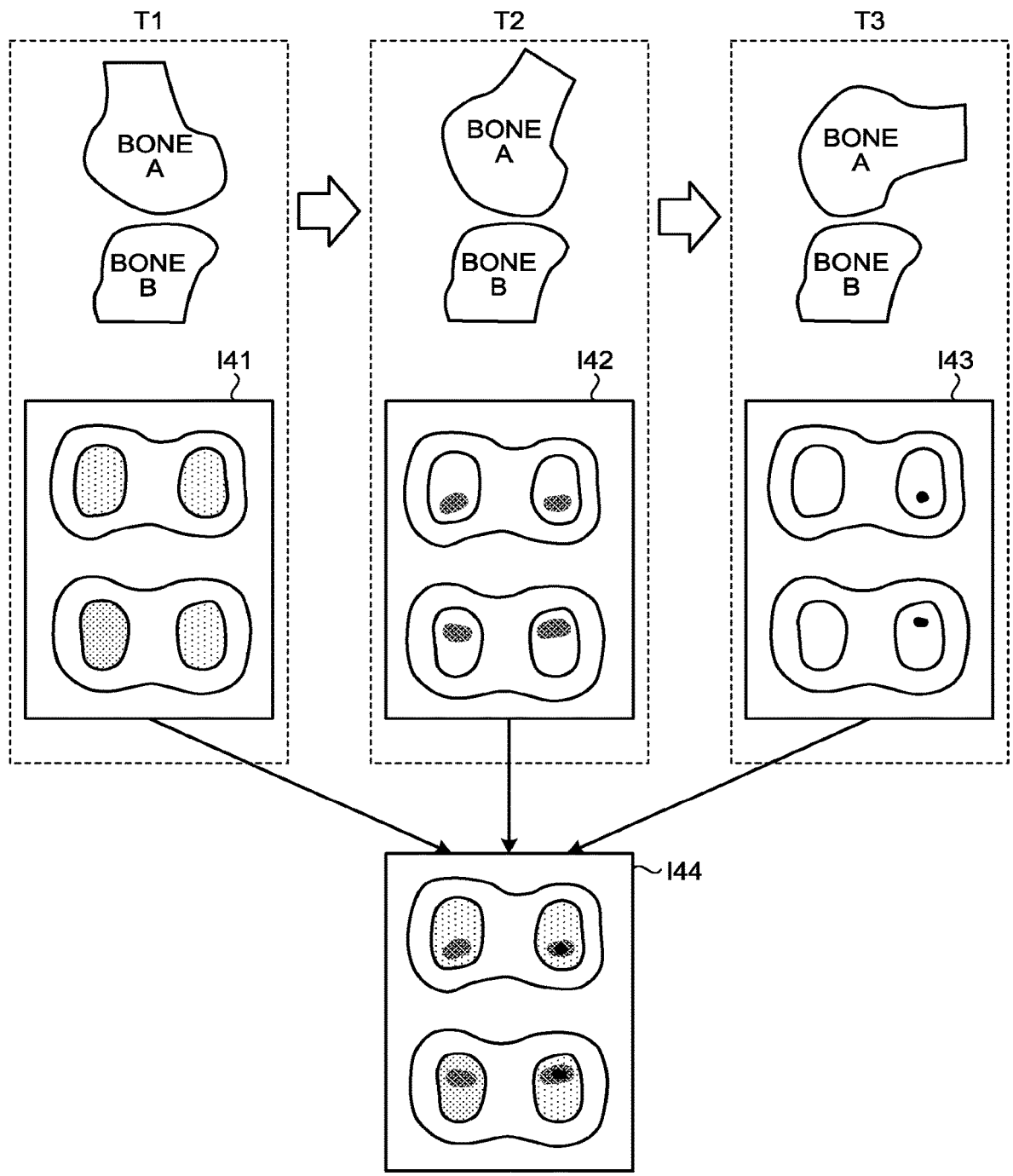
FIG. 15 is a drawing for explaining a process performed by a medical image processing apparatus according to a third modification example.

FIG. 15 is a drawing for explaining a process performed by the medical image processing apparatus 100 according to a third modification example. With reference to FIG. 15, an example will be explained in which 4D CT image data obtained by imaging a movement to inflect a knee joint is used as data subject to the analysis. The top section of FIG. 15 illustrates a manner in which the bone A (the femur) and the bone B (the tibia) are brought into inflection, in the order of temporal phases T1, T2, and T3.

In FIG. 15, the generating function 113 generates an image I41 represented by display-purpose image data in the temporal phase T1, another image I42 represented by display-purpose image data in the temporal phase T2, and yet another image I43 represented by the display-purpose image data in the temporal phase T3. Because the processes of generating the images I41, I42, and I43 are the same as the process of generating the image I10, the explanations thereof will be omitted.

Further, by performing a projection process on the images I41, I42, and I43 while implementing a sum projection method, the generating function 113 generates a ray summation image I44. In this situation, the image does not necessarily have to be the ray summation image I44, and the generating function 113 may generate a Maximum Intensity Projection (MIP) image, by performing a projection process on the images I41, I42, and I43 while implementing a maximum intensity projection method. Alternatively, the generating function 113 may generate a Minimum Intensity Projection (MinIP) image, by performing a projection process on the images I41, I42, and I43 while implementing a minimum intensity projection method.

Fourth Modification Example

Further, the index values do not necessarily have to be values indicating the degrees of bone intervals. For example, it is also acceptable to map values indicating characteristics of a bone region. The index values indicating characteristics of the bone region are examples of the second index value.

Figure 16:
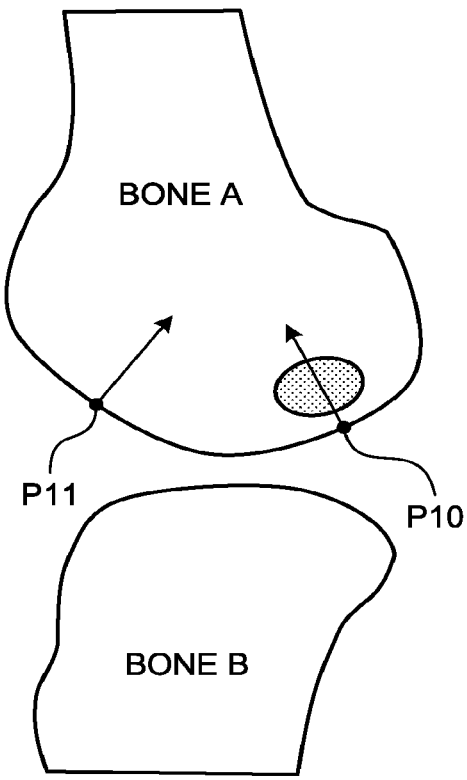
FIG. 16 is a drawing for explaining a process performed by a medical image processing apparatus according to a fourth modification example.

FIG. 16 is a drawing for explaining a process performed by the medical image processing apparatus 100 according to a fourth modification example. To explain, FIG. 16 uses a cross-sectional view represented by X-ray CT image data depicting a knee joint. In FIG. 16, the hatching region inside the bone A represents a part having a lower bone density. The higher the bone density is, the larger are the CT values. Conversely, the lower the bone density is, the smaller are the CT values.

As illustrated in FIG. 16, for example, with respect to each of the points P10 and P11, the generating function 113 is configured to calculate an index value indicating a bone density. More specifically, the generating function 113 is configured to draw a perpendicular line having a predetermined length, from each of the points toward the interior of the bone region and to calculate the index value indicating the bone density on the basis of a total value of the CT values on each of the perpendicular lines. After that, the generating function 113 is configured to map the calculated index values on one selected from between: a flat plane obtained by extending an intra-joint plane; and the surface of the bone region resulting from reshaping.

The index values explained with reference to FIG. 16 are merely examples. The index values indicating characteristics of the bone region do not necessarily have to be bone density values. For instance, the generating function 113 may calculate thicknesses of the bone cortex, as index values indicating characteristics of the bone region. The bone cortex is the extremely hard part that is present at the contour of the bone region. For this reason, the generating function 113 identifies the region of the bone cortex on the basis of characteristic information based on position information of the vicinity of the contour of the bone region and the CT values in these positions and is thus able to measure the distances in the direction of perpendicular lines in the identified region as the "thicknesses of the bone cortex".

Other Embodiments

The present disclosure may be carried out in various different modes other than those described in the above embodiments.

A Medical Image Diagnosis Apparatus

In the above embodiments, the example was explained in which the processing functions according to the embodiments are provided in the medical image processing apparatus 100; however, possible embodiments are not limited to this example. For instance, the processing functions according to the embodiments may be provided in a medical image diagnosis apparatus.

Figure 17:
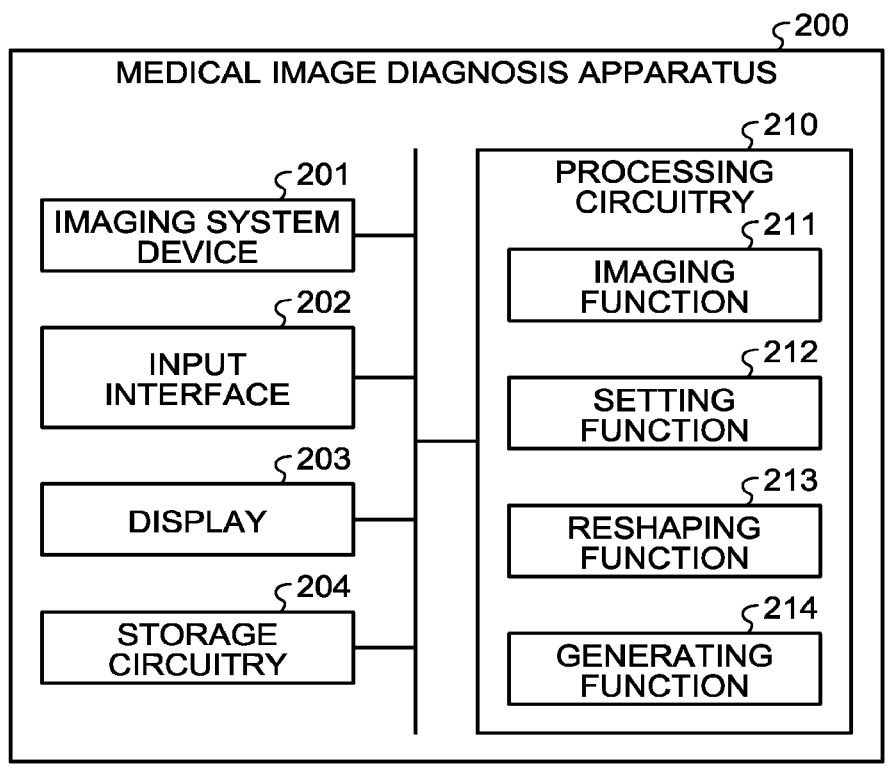
FIG. 17 is a block diagram illustrating an exemplary configuration of a medical image diagnosis apparatus according to another embodiment.

FIG. 17 is a block diagram illustrating an exemplary configuration of a medical image diagnosis apparatus according to another embodiment. As illustrated in FIG. 17, a medical image diagnosis apparatus 200 includes an imaging system device 201, an input interface 202, a display 203, storage circuitry 204, and processing circuitry 210. The imaging system device 201, the input interface 202, the display 203, the storage circuitry 204, and the processing circuitry 210 are connected to one another. Because the input interface 202, the display 203, and the storage circuitry 204 in FIG. 17 are the same as the input interface 101, the display 102, and the storage circuitry 103 illustrated in FIG. 1, explanations thereof will be omitted.

The imaging system device 201 includes devices for imaging the inside of the patient. For example, when the medical image diagnosis apparatus is an X-ray CT apparatus, the imaging system device 201 includes a gantry device having an X-ray tube and an X-ray detector, as well as a couch device for placing the patient in an image taking space.

The processing circuitry 210 is configured to execute an imaging function 211, a setting function 212, a reshaping function 213, and a generating function 214. Because the setting function 212, the reshaping function 213, and the generating function 214 are the same as the setting function 111, the reshaping function 112, and the generating function 113 illustrated in FIG. 1, explanations thereof will be omitted.

The imaging function 211 is configured to take medical image data of the patient, by controlling the imaging system device 201. For example, by controlling various types of devices included in the gantry device, the imaging function 211 is configured to acquire projection data obtained by detecting X-rays that have passed through the patient. Further, the imaging function 211 is configured to generate X-ray CT image data by performing a reconstructing process using a filter back projection method or a successive approximation reconstruction method, on the acquired projection data. The X-ray CT image data is saved in the storage circuitry 204 so as to be used in the processing functions of the setting function 212, the reshaping function 213, and the generating function 214.

As explained above, the medical image diagnosis apparatus 200 includes the function to image the inside of the patient and is also configured to execute the processing functions of the setting function 212, the reshaping function 213, and the generating function 214 by using the taken X-ray CT image data. With these arrangements, the medical image diagnosis apparatus 200 is able to enhance browsability of the joint.

Provision as a Cloud Service

The processing functions according to the above embodiments may be provided as an information processing service (a cloud service) via a network.

Figure 18:
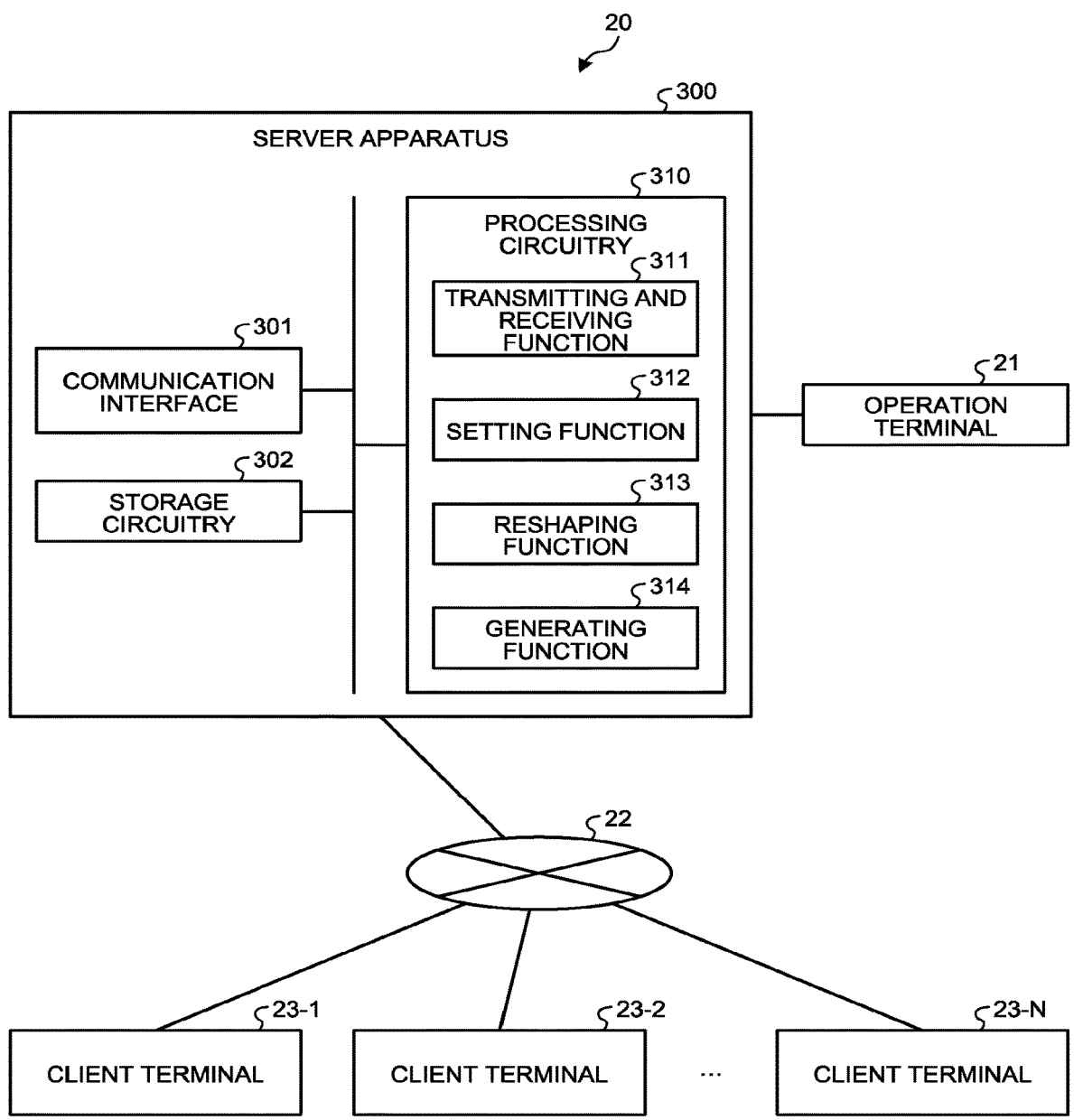
FIG. 18 is a block diagram illustrating an exemplary configuration of a medical image processing system according to yet another embodiment.

FIG. 18 is a block diagram illustrating an exemplary configuration of a medical image processing system according to yet another embodiment. A medical image processing system 20 includes an operation terminal 21, a network 22, a plurality of client terminals 23-1, 23-2, . . . , and 23-N, and a server apparatus 300. Although possible configurations of the medical image processing system 20 are not limited to the configuration in the present example, the medical image processing system 20 includes at least the client terminals 23-1, 23-2, . . . , and 23-N and the server apparatus 300.

As illustrated in FIG. 18, for example, at a service center configured to provide an information processing service, the server apparatus 300 is installed. The server apparatus 300 is connected to the operation terminal 21. Also, the server apparatus 300 is connected to the plurality of client terminals 23-1, 23-2, . . . , and 23-N via the network 22. Alternatively, the server apparatus 300 and the operation terminal 21 may be connected to each other via the network 22. When being collectively referred to without being distinguished from one another, the plurality of client terminals 23-1, 23-2, . . . , and 23-N may be referred to as "client terminals 23".

The operation terminal 21 is an information processing terminal used by a person (an operator) who operates the server apparatus 300. For example, the operation terminal 21 includes an input device configured to receive various types of instructions and setting requests from the operator, such as a mouse, a keyboard, a touch panel, and/or the like. Further, the operation terminal 21 includes a display device configured to display images and to display a GUI used by the operator to input various types of setting requests through the input device. By operating the operation terminal 21, the operator is able to transmit the various types of instructions and setting requests to the server apparatus 300 and to browse information in the server apparatus 300. Further, the network 22 is an arbitrary communication network such as the Internet, a Wide Area Network (WAN), a Local Area Network (LAN), or the like.

Each of the client terminals 23 is an information processing terminal operated by a user who uses the information processing service. In the present example, the user is, for example, a medical provider such as a medical doctor or a medical technologist who works at a medical institution. For example, each of the client terminals 23 corresponds to an information processing apparatus such as a personal computer or a workstation or an operation terminal of a medical image diagnosis apparatus such as a console device included in an MRI apparatus. Each of the client terminals 23 has a client function capable of using the information processing service provided by the server apparatus 300. The client function is recorded, in advance, in each of the client terminals 23 in the form of a computer-executable program.

The server apparatus 300 includes a communication interface 301, storage circuitry 302, and processing circuitry 310. The communication interface 301, the storage circuitry 302, and the processing circuitry 310 are communicably connected to one another.

For example, the communication interface 301 is a network card or a network adaptor. By connecting to the network 22, the communication interface 301 realizes information communication between the server apparatus 300 and external devices.

For example, the storage circuitry 302 is a Not AND (NAND) flash memory or a Hard Disk Drive (HDD) and is configured to store therein various types of programs used for displaying medical image data and GUIs, as well as information used by the programs.

The processing circuitry 310 is an electronic device (a processor) configured to control the entire processes performed by the server apparatus 300. The processing circuitry 310 is configured to execute a transmitting and receiving function 311, a setting function 312, a reshaping function 313, and a generating function 314. Because the setting function 312, the reshaping function 313, and the generating function 314 are the same as the setting function 111, the reshaping function 112, and the generating function 113 illustrated in FIG. 1, explanations thereof will be omitted.

For example, by operating any one of the client terminals 23, a user inputs an instruction indicating that medical image data be transmitted (uploaded) to the server apparatus 300 provided at the service center. When the instruction indicating that the medical image data be transmitted has been input, the client terminal 23 transmits the medical image data to the server apparatus 300.

Further, in the server apparatus 300, the transmitting and receiving function 311 receives the medical image data transmitted from the client terminal 23. Further, the processing functions, namely, the setting function 312, the reshaping function 313, and the generating function 314, perform the processes according to the above embodiment, by using the received medical image data. After that, the transmitting and receiving function 311 transmits the display-purpose image data generated by the generating function 314 to the client terminal 23 (causes the display-purpose image data to be downloaded). As a result, the server apparatus 300 is able to enhance browsability of the joint.

The configuration explained with reference to FIG. 18 is merely an example, and possible embodiments are not limited to this example. For instance, one or more arbitrary processing functions among the setting function 312, the reshaping function 313, and the generating function 314 included in the server apparatus 300 may be provided in the client terminals 23.

In other words, the medical image processing system 20 includes the terminal (the client terminals 23) operated by an operator and the server apparatus 300 capable of communicating with the terminal. In the medical image processing system 20, the setting function 312 is configured to set a curved plane between the first bone region and the second bone region included in the joint, in the three-dimensional medical image data. The reshaping function 313 is configured to reshape at least one of the first and the second bone regions, along extension of the intra-joint plane. The generating function 314 is configured to generate the display-purpose image data on the basis of the reshaped bone region. With these arrangements, the medical image processing system 20 is able to enhance browsability of the joint, without imposing loads on the client terminals 23.

Further, the constituent elements of the apparatuses and devices in the drawings are based on functional concepts. Thus, it is not necessary to physically configure the constituent elements as indicated in the drawings. In other words, specific modes of distribution and integration of the apparatuses and devices are not limited to those illustrated in the drawings. It is acceptable to functionally or physically distribute or integrate all or a part of the apparatuses and devices in any arbitrary units, depending on various loads and the status of use. Further, all or an arbitrary part of the processing functions performed by the apparatuses and devices may be realized by a CPU and a program analyzed and executed by the CPU or may be realized as hardware using wired logic.

With regard to the processes explained in the embodiments and modification examples described above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

Further, it is possible to realize the medical image processing methods explained in the above embodiments and modification examples, by causing a computer such as a personal computer or a workstation to execute a medical image processing program prepared in advance. The medical image processing program may be distributed via a network such as the Internet. Further, the medical image processing program may be executed, as being recorded on a computer-readable recording medium such as a hard disk, a flexible disk (FD), a Compact Disk Read-Only Memory (CD-ROM), a Magneto Optical (MO) disk, a Digital Versatile Disk (DVD), or the like and being read by a computer from the recording medium.

According to at least one aspect of the embodiments described above, it is possible to enhance browsability of the joint.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured:
to set a curved plane between a first bone region and a second bone region included in a joint, in three-dimensional medical image data obtained by imaging the joint including at least the first bone region and the second bone region;
to planarly reshape at least one of the first and the second bone regions along extension of the curved plane to obtain a reshaped bone region; and
to generate display-purpose image data on a basis of the reshaped bone region resulting from the planarly reshaping.

2. The medical image processing apparatus according to claim 1, wherein, as the display-purpose image data, the processing circuitry generates image data obtained by mapping a first index value indicating a degree of an interval between the first bone region and the second bone region, on one selected from between: a flat plane obtained by extending the curved plane; and a surface of the reshaped bone region.

3. The medical image processing apparatus according to claim 2, wherein, as the first index value, the processing circuitry calculates at least one of: a distance to a surface of an opposing bone region; a longest distance between the bone regions among a plurality of temporal phases; a shortest distance between the bone regions among a plurality of temporal phases; an average distance between the bone regions among a plurality of temporal phases; a length of time during which the distance between the bone regions is equal to or shorter than a threshold value among a plurality of temporal phases; and a difference in bone region distances between mutually-different temporal phases.

4. The medical image processing apparatus according to claim 1, wherein, as the display-purpose image data, the processing circuitry generates image data obtained by mapping a second index value indicating characteristics of the bone region, on one selected from between: a flat plane obtained by extending the curved plane; and a surface of the reshaped bone region.

5. The medical image processing apparatus according to claim 1, wherein, in the display-purpose image data, the processing circuitry displays identification information for identifying a bone opposing a depicted bone.

6. The medical image processing apparatus according to claim 1, wherein, from the first and the second bone regions, the processing circuitry identifies proximate regions that are present within a predetermined distance from each other and sets the curved plane in a middle of the proximate region from the first bone region and the proximate region from the second bone region.

7. The medical image processing apparatus according to claim 6, wherein the processing circuitry reshapes the proximate regions along the extension of the curved plane, but does not reshape regions other than the proximate regions.

8. The medical image processing apparatus according to claim 1, wherein the processing circuitry receives an input operation from an operator designating an arbitrary region in the first and the second bone regions and reshapes a region other than the designated region, without reshaping the designated region.

9. The medical image processing apparatus according to claim 1, wherein the medical image processing apparatus is a medical image diagnosis apparatus.

10. A medical image processing system including a terminal operated by an operator and a server apparatus capable of communicating with the terminal, the medical image processing system comprising processing circuitry configured:
to set a curved plane between a first bone region and a second bone region included in a joint, in three-dimensional medical image data obtained by imaging the joint including at least the first bone region and the second bone region;

to planarly reshape at least one of the first and the second bone regions along extension of the curved plane to obtain a reshaped bone region; and to generate display-purpose image data on a basis of the reshaped bone region resulting from the planarly reshaping.

11. A computer program product which includes a non-transitory computer-readable recording medium comprising a plurality of computer-executable instructions that cause a computer to execute:

setting a curved plane between a first bone region and a second bone region included in a joint, in three-dimensional medical image data obtained by imaging the joint including at least the first bone region and the second bone region;

planarly reshaping at least one of the first and the second bone regions along extension of the curved plane to obtain a reshaped bone region; and generating display-purpose image data on a basis of the reshaped bone region resulting from the planarly reshaping.

12. A medical image processing method comprising:

setting a curved plane between a first bone region and a second bone region included in a joint, in three-dimensional medical image data obtained by imaging the joint including at least the first bone region and the second bone region;

planarly reshaping at least one of the first and the second bone regions along extension of the curved plane to obtain a reshaped bone region; and generating display-purpose image data on a basis of the reshaped bone region resulting from the planarly reshaping.

* * * * *